United States Patent
Iwama

(10) Patent No.: US 12,085,643 B2
(45) Date of Patent: Sep. 10, 2024

(54) TRANSMISSION CIRCUIT AND ULTRASOUND DIAGNOSIS APPARATUS

(71) Applicant: CANON MEDICAL SYSTEMS CORPORATION, Otawara (JP)

(72) Inventor: Nobuyuki Iwama, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 801 days.

(21) Appl. No.: 17/209,644

(22) Filed: Mar. 23, 2021

(65) Prior Publication Data
US 2021/0302575 A1    Sep. 30, 2021

(30) Foreign Application Priority Data

Mar. 24, 2020 (JP) .................. 2020-052578

(51) Int. Cl.
G01S 15/89 (2006.01)
A61B 8/00 (2006.01)
G01S 7/52 (2006.01)
B06B 1/02 (2006.01)

(52) U.S. Cl.
CPC ............... *G01S 15/89* (2013.01); *A61B 8/42* (2013.01); *A61B 8/4444* (2013.01); *G01S 7/52001* (2013.01); *G01S 7/5202* (2013.01); *G01S 7/5208* (2013.01); *B06B 1/0207* (2013.01);
(Continued)

(58) Field of Classification Search
CPC .................................................. B06B 1/0207
See application file for complete search history.

(56) References Cited

U.S. PATENT DOCUMENTS

2010/0087737 A1    4/2010  Iwama et al.
2010/0331703 A1    12/2010 Amemiya
(Continued)

FOREIGN PATENT DOCUMENTS

JP      9-234202 A      9/1997
JP      2000-152930 A   6/2000
(Continued)

OTHER PUBLICATIONS

Assef et al., "A Reconfigurable Arbitrary Waveform Generator Using PWM Modulation for Ultrasound Research" BioMedical Engineering OnLine 2013, 12:24 http://www.biomedical-engineering-online.com/content/12/1/24, 13 pages.
(Continued)

*Primary Examiner* — Bryan P Gordon
(74) *Attorney, Agent, or Firm* — Oblon, McClelland, Maier & Neustadt, L.L.P.

(57) ABSTRACT

A transmission circuit according to an embodiment includes: a plurality of constant current circuits, a plurality of switching elements, and controlling circuitry. The plurality of constant current circuits are connected in parallel to a power source line connected to a single power source and a transducer element. Each of the plurality of switching elements is connected to a different one of the plurality of constant current circuits and to the transducer element. The controlling circuitry is configured to control the plurality of switching elements on the basis of a waveform signal indicating a waveform of an ultrasound wave output from the transducer element.

6 Claims, 5 Drawing Sheets

(52) U.S. Cl.
CPC ....... *G01S 7/52017* (2013.01); *G01S 15/8906* (2013.01)

(56) References Cited

U.S. PATENT DOCUMENTS

| | | | | |
|---|---|---|---|---|
| 2012/0218135 | A1* | 8/2012 | Amemiya | H03M 1/66 |
| | | | | 341/144 |
| 2014/0232241 | A1* | 8/2014 | Hajati | G01N 29/262 |
| | | | | 310/317 |
| 2015/0345987 | A1* | 12/2015 | Hajati | G01N 29/34 |
| | | | | 73/661 |
| 2016/0106393 | A1* | 4/2016 | Kameishi | B06B 1/0607 |
| | | | | 600/459 |
| 2017/0065258 | A1* | 3/2017 | Passi | G01S 15/8915 |

FOREIGN PATENT DOCUMENTS

| | | |
|---|---|---|
| JP | 2007-503242 A | 2/2007 |
| JP | 2008-194290 A | 8/2008 |
| JP | 2010-82350 A | 4/2010 |
| JP | 2011-4998 A | 1/2011 |
| JP | 2012-176235 A | 9/2012 |
| JP | 2018-110713 A | 7/2018 |
| WO | WO 2010/101104 A1 | 9/2010 |

OTHER PUBLICATIONS

Reeder, "Integrated Components Offer Flexibility In Ultrasound System Design" Technical Article MS-1849, Oct. 2010, 4 pages.

Boni, et al., "Ultrasound Open Platforms for Next-Generation Imaging Technique Development" IEEE Transactions on Ultrasonics, Ferroelectrics, and Frequency Control, vol. 65, No. 7, Jul. 2018, 15 pages.

"Ultrasound Imaging" STMicroelectronics, https://www.st.com/en/applications/medical-and-healthcare/ultrasound-imaging.html, Jan. 20, 2020, 2 pages.

Japanese Office Action issued on Sep. 12, 2023 in Japanese Patent Application No. 2020-052578, citing documents 15-16 therein, 3 pages.

* cited by examiner

TRANSMISSION CIRCUIT AND ULTRASOUND DIAGNOSIS APPARATUS

CROSS-REFERENCE TO RELATED APPLICATIONS

This application is based upon and claims the benefit of priority from Japanese Patent Application No. 2020-052578, filed on Mar. 24, 2020; the entire contents of which are incorporated herein by reference.

FIELD

Embodiments described herein relate generally to a transmission circuit and an ultrasound diagnosis apparatus.

BACKGROUND

To realize higher harmonic imaging, transmission waiting control, or the like, high-end (high class) ultrasound diagnosis apparatuses use a linear amplifier capable of outputting a signal (a drive signal) having an arbitrary waveform. For example, to output a pulse with high voltage of 100 V or higher, it is necessary to cause a large bias current to flow in an amplifying circuit included in the linear amplifier, which involves large power consumption.

Further, because the signals handled by the linear amplifier are signals in an analog format (analog signals), a Digital-to-Analog Converter (DAC) circuit configured to convert a waveform signal in a digital format into a waveform signal in an analog format is provided at a stage preceding the linear amplifier. The DAC circuit is large in size (circuit scale) and has a high cost (being expensive).

DETAILED DESCRIPTION

A transmission circuit according to an embodiment includes: a plurality of constant current circuits, a plurality of switching elements, and controlling circuitry. The plurality of constant current circuits are connected in parallel to a power source line connected to a single power source and a transducer element. Each of the plurality of switching elements is connected to a different one of the plurality of constant current circuits and to the transducer element. The controlling circuitry is configured to control the plurality of switching elements on the basis of a waveform signal indicating a waveform of an ultrasound wave output from the transducer element.

Exemplary embodiments of a transmission circuit and an ultrasound diagnosis apparatus will be explained below, with reference to the accompanying drawings. The description of each of the embodiments and the modification examples is similarly applicable to any other embodiment or any other modification example.

First Embodiment

Figure 1:
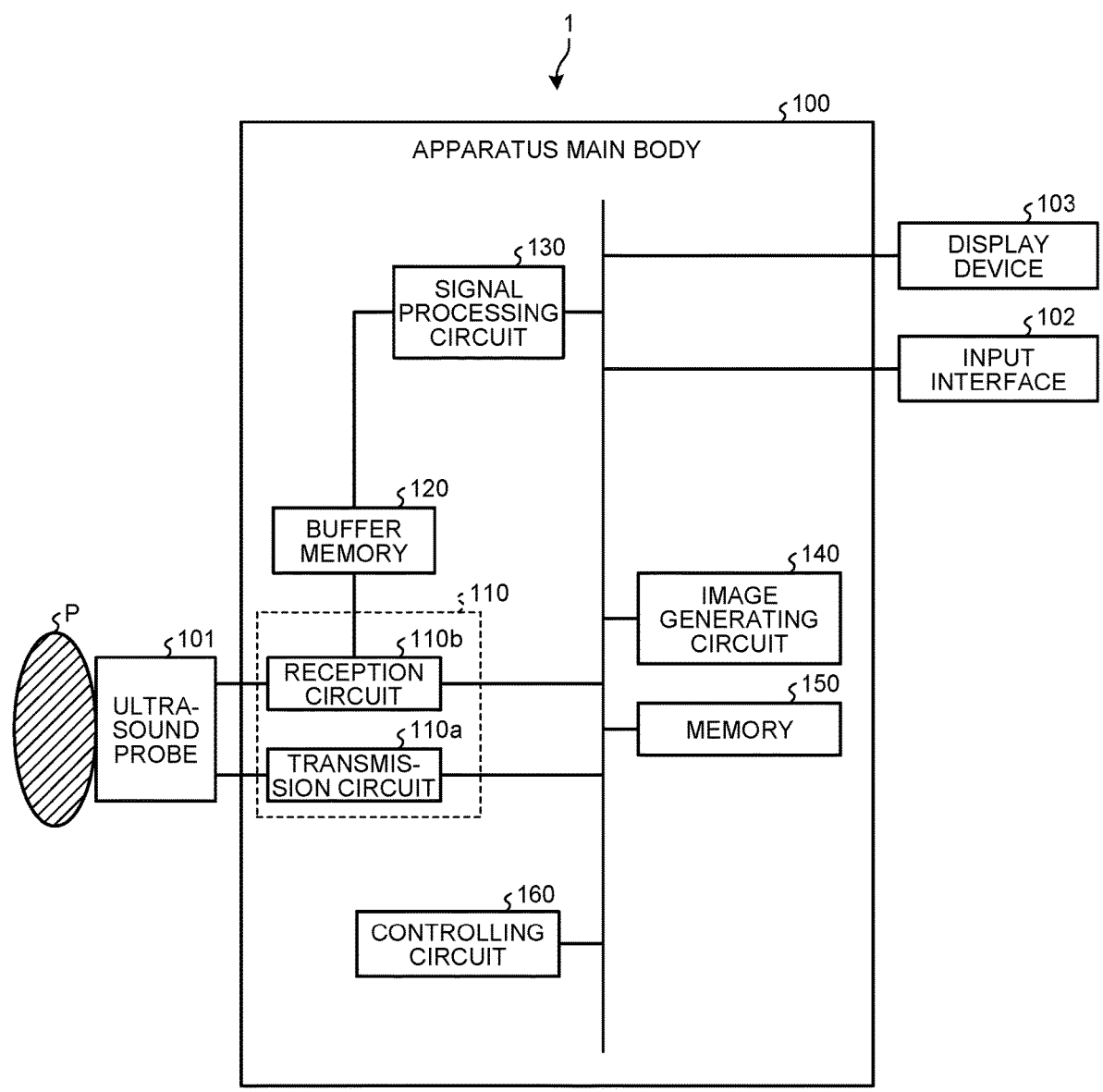
FIG. 1 is a bloc diagram illustrating an exemplary configuration of an ultrasound diagnosis apparatus according to an embodiment.

FIG. 1 is a block diagram illustrating an exemplary configuration of an ultrasound diagnosis apparatus 1 according to a first embodiment. As illustrated in FIG. 1, the ultrasound diagnosis apparatus 1 according to the first embodiment includes an apparatus main body 100, an ultrasound probe 101, an input interface 102, and a display device 103.

For example, the ultrasound probe 101 includes a plurality of transducer elements such as piezoelectric transducer elements. Each of the plurality of transducer elements is configured to generate an ultrasound wave on the basis of a drive signal supplied thereto from a transmission circuit 110a of a transmission and reception circuit 110 included in the apparatus main body 100. Further, the ultrasound probe 101 is configured to receive reflected waves from an examined subject (hereinafter "patient") P, to convert the received reflected waves into reflected-wave signals each being an electrical signal, and to output the reflected-wave signals to the apparatus main body 100. Further, for example, the ultrasound probe 101 includes a matching layer provided for the transducer elements, a backing member that prevents the ultrasound waves from propagating rearward from the transducer elements, and the like. The ultrasound probe 101 is detachably connected to the apparatus main body 100.

When an ultrasound wave is transmitted from the ultrasound probe 101 to the patient P, the transmitted ultrasound wave is repeatedly reflected on a surface of discontinuity of acoustic impedances at a tissue in the body of the patient P and is received as a reflected wave by the plurality of transducer elements included in the ultrasound probe 101. The amplitude of the received reflected wave is dependent on the difference between the acoustic impedances on the surface of discontinuity on which the ultrasound wave is reflected. When a transmitted ultrasound pulse is reflected on the surface of a moving blood flow, a cardiac wall, or the like, the reflected wave is, due to the Doppler effect, subject to a frequency shift, depending on a velocity component of the moving members with respect to the ultrasound wave transmission direction. Further, the ultrasound probe 101 is configured to output the reflected-wave signals to a reception circuit 110b of the transmission and reception circuit 110 (explained later).

The ultrasound probe 101 is provided so as to be attachable to and detachable from the apparatus main body 100. When a two-dimensional region in the patient P is to be scanned (a two-dimensional scan), the user connects, for example, a one-dimensional (1D) array probe in which the plurality of transducer elements are arranged in a row to the apparatus main body 100 as the ultrasound probe 101. Possible types of the 1D array probe include a linear ultrasound probe, a convex ultrasound probe, and a sector ultrasound probe. In contrast, when a three-dimensional region in the patient P is to be scanned (a three-dimensional scan), the user connects, for example, a mechanical four-dimensional (4D) probe or a two-dimensional (2D) array probe to the apparatus main body 100 as the ultrasound probe 101. The mechanical 4D probe is capable of performing a two-dimensional scan by using the plurality of transducer elements arranged in a row similarly to those in the 1D array probe and is also capable of performing a three-dimensional scan by swinging the plurality of transducer elements at a predetermined angle (a swinging angle). Further, the 2D array probe is capable of performing a three-dimensional scan by using the plurality of transducer elements arranged in a matrix formation and is capable of performing a two-dimensional scan by converging and transmitting ultrasound waves.

The input interface 102 is realized by input means such as, for example, a mouse, a keyboard, a button, a panel switch, a touch command screen, a foot switch, a trackball, a joystick, and/or the like. The input interface 102 is configured to receive various types of setting requests from a user of the ultrasound diagnosis apparatus 1 and to transfer the received various types of setting requests to the apparatus main body 100.

The display device 103 is configured, for example, to display a Graphical User Interface (GUI) used by the user of the ultrasound diagnosis apparatus 1 for inputting the various types of setting requests through the input interface 102 and to display an ultrasound image based on ultrasound image data generated by the apparatus main body 100 and the like. The display device 103 is realized by using a liquid crystal monitor, a Cathode Ray Tube (CRT) monitor, or the like.

The apparatus main body 100 is configured to generate the ultrasound image data on the basis of the reflected-wave signals transmitted thereto from the ultrasound probe 101. The ultrasound image data is an example of image data. The apparatus main body 100 is capable of generating two-dimensional ultrasound image data on the basis of reflected-wave signals corresponding to a two-dimensional region of the patient P and being transmitted thereto from the ultrasound probe 101. Further, the apparatus main body 100 is also capable of generating three-dimensional ultrasound image data on the basis of reflected-wave signals corresponding to a three-dimensional region of the patient P and being transmitted thereto from the ultrasound probe 101. As illustrated in FIG. 1, the apparatus main body 100 includes the transmission and reception circuit 110, a buffer memory 120, a signal processing circuit (signal processing circuitry) 130, an image generating circuit (image generating circuitry) 140, a memory 150, and a controlling circuit (controlling circuitry) 160.

Under control of the controlling circuit 160, the transmission and reception circuit 110 is configured to cause the ultrasound waves to be transmitted from the ultrasound probe 101 and to cause the ultrasound waves (the reflected waves of the ultrasound waves) to be received by the ultrasound probe 101. In other words, the transmission and reception circuit 110 is configured to perform a scan via the ultrasound probe 101. The scanning may be referred to as a scan, an ultrasound scan, or ultrasound scanning. The transmission and reception circuit 110 is an example of a transmitting and receiving unit. The transmission and reception circuit 110 includes the transmission circuit 110a and the reception circuit 110b.

Under the control of the controlling circuit 160, the transmission circuit 110a is configured to cause the ultrasound waves to be transmitted from the ultrasound probe 101. The transmission circuit 110a is configured to supply the drive signal (a transmission pulse of the drive signal) to the ultrasound probe 101. When a two-dimensional region in the patient P is to be scanned, the transmission circuit 110a is configured to cause an ultrasound beam for scanning the two-dimensional region to be transmitted from the ultrasound probe 101. In another example, when a three-dimensional region in the patient P is to be scanned, the transmission circuit 110a is configured to cause an ultrasound beam for scanning the three-dimensional region to be transmitted from the ultrasound probe 101. The transmission circuit 110a will be explained later.

The transmission circuit 110a has a function of performing a prescribed delay process on the drive signal and supplying the drive signal on which the prescribed delay process has been performed to the transducer elements. In the present embodiment, for example, one channel is assigned to each of the transducer elements, so that the prescribed delay process is performed on the drive signal with respect to each of the channels. As a result, the transmission circuit 110a is configured, for example, to control transmission directionality of the ultrasound waves by converging the ultrasound waves emitted from the transducer elements into a beam form.

The reflected waves of the ultrasound waves transmitted by the ultrasound probe 101 reach the transducer elements provided inside the ultrasound probe 101 and are subsequently converted from mechanical vibration into the electrical signals (the reflected-wave signals) at the transducer elements, before being input to the reception circuit 110b. The reception circuit 110b includes a pre-amplifier, an Analog-to-Digital (A/D) converter, a reception delay circuit, an adder, and the like and is configured to generate reflected-wave data by performing various types of processes on the reflected-wave signals transmitted thereto from the ultrasound probe 101. After that, the reception circuit 110b is configured to store the generated reflected-wave data into the buffer memory 120.

The pre-amplifier is configured to make a gain adjustment (a gain correction) by amplifying the reflected-wave signal with respect to each of the channels. The A/D converter is configured to convert the gain-corrected reflected-wave signals into digital signals, by performing an A/D conversion on the gain-corrected reflected-wave signals. The reception delay circuit is configured to apply a delay time period necessary for determining reception directionality, to the reflected-wave signals that were converted into the digital signal.

The adder is configured to generate the reflected-wave data (a Radio Frequency [RF] signal) by performing an adding process on the reflected-wave signals processed by the reception delay circuit. After that the adder is configured to store the reflected-wave data into the buffer memory 120. As described herein, in the present embodiment, the reception delay circuit and the adder perform a phased addition process. In the present embodiment, for example, one channel is assigned to each of the transducer elements. Further, the reception delay circuit is configured to apply the delay time period to the reflected-wave signal of each of the channels, whereas the adder is configured to perform the adding process of adding together the plurality of reflected-wave signals to which the delay time periods were applied by the reception delay circuit.

The reception circuit 110b is configured to generate two-dimensional reflected-wave data from the two-dimensional reflected-wave signals transmitted thereto from the ultrasound probe 101. In another example, the reception circuit 110b is configured to generate three-dimensional reflected-wave data from the three-dimensional reflected-wave signals transmitted thereto from the ultrasound probe 101.

The buffer memory 120 is a memory configured to temporarily store therein the reflected-wave data generated by the transmission and reception circuit 110. For example, under control of the reception circuit 110*b*, the buffer memory 120 is configured to be able to store therein a prescribed number of pieces of reflected-wave data each corresponding to one frame. Further, while having stored therein the prescribed number of pieces of reflected-wave data each corresponding to one frame, when another piece of reflected-wave data corresponding to one frame is newly generated by the reception circuit 110*b*, the buffer memory 120 is configured, under the control of the reception circuit 110*b*, to discard a piece of reflected-wave data corresponding to one frame that was generated earliest and to store therein the newly-generated piece of reflected-wave data corresponding to the one frame. For example, the buffer memory 120 is realized by using a semiconductor memory element such as a Random Access Memory (RAM) or a flash memory.

The signal processing circuit 130 is configured to read the reflected-wave data from the buffer memory 120, to perform various types of signal processing processes on the read reflected-wave data, and to output the reflected-wave data on which the various types of signal processing processes have been performed to the image generating circuit 140 as B-mode data or Doppler data. The signal processing circuit 130 is realized by using a processor, for example. The signal processing circuit 130 is an example of a signal processing unit.

For example, the signal processing circuit 130 is configured to generate B-mode data in which the signal intensity (amplitude intensity) at each sampling point is expressed by a degree of brightness, by performing an orthogonal detection as well as a logarithmic amplification, an envelope detecting process, and/or the like on the reflected-wave data read from the buffer memory 120. For example, the signal processing circuit 130 is configured to output the generated B-mode data to the image generating circuit 140.

Further, the signal processing circuit 130 is configured to perform a signal processing process to realize harmonic imaging by which a higher harmonic component is visualized in an image. Examples of the harmonic imaging include Contrast Harmonic Imaging (CHI) and Tissue Harmonic Imaging (THI). Further, for the contrast harmonic imaging and the tissue harmonic imaging, the following scan methods are known, for example: Amplitude Modulation (AM) methods, Phase Modulation (PM) methods called a pulse subtraction method and a pulse inversion method, and AMPM methods in which advantageous effects of both the AM and the PM methods are achieved by combining the AM and the PM methods together.

The signal processing circuit 130 is configured to extract movement information of moving members (a blood flow, a tissue, a contrast agent echo component, and/or the like) based on the Doppler effect from the reflected-wave data, by performing a frequency analysis on the reflected-wave data read from the buffer memory 120 and to generate Doppler data indicating the extracted movement information. For example, the signal processing circuit 130 is configured to generate the Doppler data indicating the extracted movement information of the moving members, by extracting, as the movement information of the moving members, an average velocity value, an average dispersion value, an average power value, and the like with respect to multiple points. The signal processing circuit 130 is configured to output the generated Doppler data to the image generating circuit 140.

By using the functions of the signal processing circuit 130 described above, the ultrasound diagnosis apparatus 1 according to an embodiment is capable of implementing a color Doppler method that may be called a Color Flow Mapping (CFM) method. According to the color flow mapping method, ultrasound wave transmission and reception is performed multiple times on a plurality of scanning lines. Further, according to the color flow mapping method, a signal (a blood flow signal) derived from a blood flow is extracted by applying a Moving Target Indicator (MTI) filter to data sequences in mutually the same position, while suppressing signals (clutter signals) derived from stationary tissues or a slow-moving tissues within the data sequences in mutually the same position. Further, according to the color flow mapping method, blood flow information such as velocity of the blood flow, dispersion of the blood flow, power of the blood flow, and the like are estimated on the basis of the blood flow signal. The signal processing circuit 130 is configured to output Doppler data indicating the blood flow information estimated by implementing the color flow mapping method, to the image generating circuit 140.

The signal processing circuit 130 is capable of processing both types of reflected-wave data, namely, the two-dimensional reflected-wave data and the three-dimensional reflected-wave data.

The image generating circuit 140 is configured to generate ultrasound image data from the B-mode data and the Doppler data output from the signal processing circuit 130. For example, the image generating circuit 140 is configured to generate two-dimensional B-mode image data in which the intensities of the reflected waves are expressed with brightness levels, from two-dimensional B-mode data generated by the signal processing circuit 130. Further, the image generating circuit 140 is configured to generate two-dimensional Doppler image data in which the movement information or the blood flow information is visualized in an image, from two-dimensional Doppler data generated by the signal processing circuit 130. The two-dimensional Doppler image data is velocity image data, dispersion image data, power image data, or image data combining together these types of image data. The image generating circuit 140 is realized by using a processor.

In this situation, generally speaking, the image generating circuit 140 is configured to convert (by performing a scan convert process) a scanning line signal sequence from an ultrasound scan into a scanning line signal sequence in a video format used by, for example, television and to generate display-purpose ultrasound image data. For example, the image generating circuit 140 is configured to generate the display-purpose ultrasound image data by performing a coordinate transformation process compliant with the ultrasound scanning mode used by the ultrasound probe 101 on the data output from the signal processing circuit 130. Further, as various types of image processing processes besides the scan convert process, the image generating circuit 140 is configured to perform, for example, an image processing process (a smoothing process) to re-generate an average brightness value image, an image processing process (an edge enhancement process) that uses a differential filter inside an image, or the like, by using a plurality of image frames resulting from the scan convert process. Also, the image generating circuit 140 is configured to combine text information of various types of parameters, scale graduations, body marks, and the like with the ultrasound image data.

Further, the image generating circuit 140 is configured to generate three-dimensional B-mode image data by performing a coordinate transformation process on three-dimensional B-mode data generated by the signal processing circuit 130. Further, the image generating circuit 140 is configured to generate three-dimensional Doppler image data by performing a coordinate transformation process on three-dimensional Doppler data generated by the signal processing circuit 130. In other words, the image generating circuit 140 is configured to generate the "three-dimensional B-mode image data and three-dimensional Doppler image data" as "three-dimensional ultrasound image data (volume data)". Further, the image generating circuit 140 is configured to perform various types of rendering processes on the volume data, so as to generate various types of two-dimensional image data used for displaying the volume data on the display device 103.

Examples of the rendering processes performed by the image generating circuit 140 include a process of generating Multi Planar Reconstruction (MPR) image data from the volume data by using a Multi Planar Reconstruction (MPR) method. Further, other examples of the rendering processes performed by the image generating circuit 140 include a Volume Rendering (VR) process by which two-dimensional image data reflecting three-dimensional information is generated. The image generating circuit 140 is an example of an image generating unit.

The B-mode data and the Doppler data are each ultrasound image data before the scan convert process. The data generated by the image generating circuit 140 is the display-purpose ultrasound image data after the scan convert process. The B-mode data and the Doppler data may be referred to as raw data.

The memory 150 is a memory configured to store therein various types of image data generated by the image generating circuit 140. Further, the memory 150 is also configured to store therein the data generated by the signal processing circuit 130. The user is able to invoke the B-mode data and the Doppler data stored in the memory 150 after a diagnosis process, for example. The invoked data serves as display-purpose ultrasound image data after being routed through the image generating circuit 140.

Further, the memory 150 is also configured to store therein control programs for performing the scan (the ultrasound wave transmission and reception), image processing processes, and display processes, as well as various types of data such as diagnosis information (e.g., patient IDs, medical doctors' observations, etc.), diagnosis protocols, and various types of body marks. For example, the memory 150 is realized by using a semiconductor memory element such as a RAM or a flash memory, a hard disk, or an optical disk.

The controlling circuit 160 is configured to control the entirety of the processes performed by the ultrasound diagnosis apparatus 1. More specifically, the controlling circuit 160 is configured to control processes performed by the transmission and reception circuit 110, the signal processing circuit 130, and the image generating circuit 140, on the basis of the various types of setting requests input from the user via the input interface 102 and the various types of control programs and various types of data read from the memory 150. Further, the controlling circuit 160 is configured to control the display device 103 so as to display ultrasound images based on the display-purpose ultrasound image data stored in the memory 150. For example, the controlling circuit 160 is realized by using a processor. The ultrasound images are examples of images.

Further, the controlling circuit 160 is configured to control the ultrasound scan by controlling the ultrasound probe 101 via the transmission and reception circuit 110.

An overall configuration of the ultrasound diagnosis apparatus 1 according to the embodiment has thus been explained. Next, an ultrasound diagnosis apparatus according to a comparison example will be explained.

For example, a known ultrasound diagnosis apparatus includes a transmission circuit configured to transmit a drive signal having a rectangular wave pulse by switching a transmission power source and an output with the use of a switch. In contrast, the ultrasound diagnosis apparatus according to a comparison example includes a transmission circuit having a linear amplifier capable of outputting a drive signal having an arbitrary waveform, for the purpose of reducing second harmonic as an image visualization method. For example, the ultrasound diagnosis apparatus according to the comparison example is a high-end ultrasound diagnosis apparatus.

For example, in the ultrasound diagnosis apparatus according to the comparison example, the transmission circuit is configured to generate and output the drive signal having a waveform of a Gaussian wave. As a result, the ultrasound diagnosis apparatus according to the comparison example is able to realize higher harmonic imaging with excellent resolution, by suppressing secondary harmonic components in the transmission. Further, the ultrasound diagnosis apparatus according to the comparison example is configured to perform various types of image visualization, for example, as a result of the transmission circuit transmitting waveform data obtained by mixing together waveform data in two frequency bands, so that image visualization is realized in a wide reception band by detecting a higher harmonic or a sum/difference component frequency thereof.

However, in the comparison example, it is necessary to cause a large bias current to flow in the amplifying circuit included in the linear amplifier in order to output a pulse having high voltage of 100 V or higher, which involves large power consumption.

Further, because the signals handled by the linear amplifier are signals in an analog format (analog signals), a Digital-to-Analog Converter (DAC) circuit configured to convert a drive signal in a digital format into a drive signal in an analog format is provided at a stage preceding the linear amplifier. The DAC circuit is large in size and has a high cost. The ultrasound diagnosis apparatus according to the comparison example has installed therein transmission circuits of which the quantity corresponds to the quantity of a large number of channels (e.g., 128 or 192), in order to drive the transducer elements. As a result, the ultrasound diagnosis apparatus is large in size and also has a high cost.

As explained above, the ultrasound diagnosis apparatus according to the comparison example has large power consumption, is large in size, and has a high cost. To cope with this situation, as explained below, the ultrasound diagnosis apparatus 1 according to the first embodiment is configured to be able to suppress power consumption, the size, and the cost.

Figure 2:
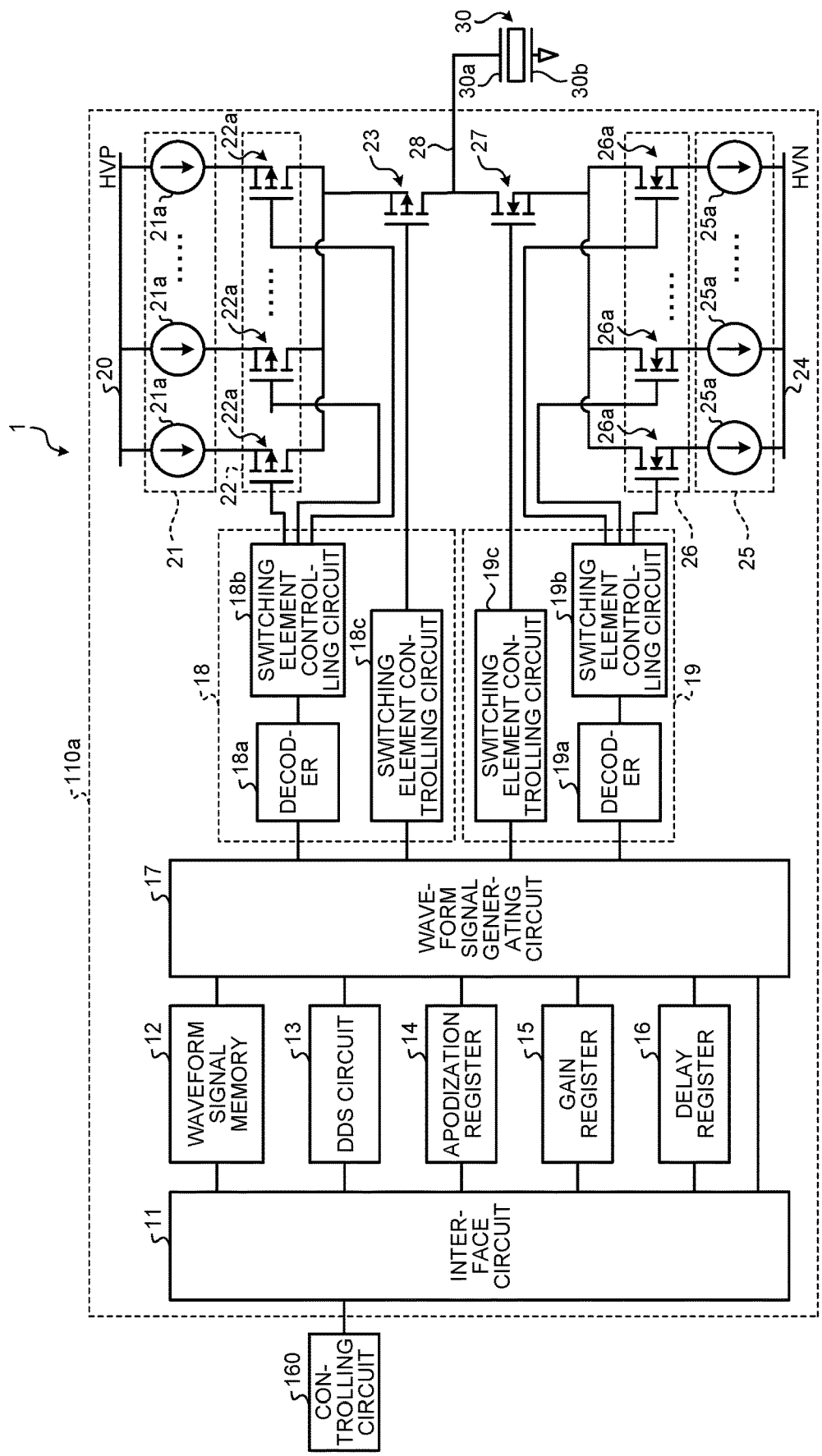
FIG. 2 is a diagram illustrating an exemplary configuration corresponding to any one of the channels in a transmission circuit according to a first embodiment.

FIG. 2 is a diagram illustrating an exemplary configuration corresponding to any one of the channels in the transmission circuit 110a in the first embodiment. Accordingly, the transmission circuit 110a includes the configuration illustrated in FIG. 2 in a quantity corresponding to the quantity of the plurality of channels.

As illustrated in FIG. 2, the transmission circuit 110a includes, with respect to each of the channels, an interface circuit 11, a waveform signal memory 12, a Direct Digital Synthesizer (DDS) circuit 13, an apodization register 14, a gain register 15, a delay register 16, a waveform signal generating circuit 17, controlling circuits (controlling circuitries) 18 and 19, power source lines (power supply lines) 20 and 24, constant current circuit groups 21 and 25, switching element groups 22 and 26, and switching elements 23 and 27. Further, as illustrated in FIG. 2, the configuration of the transmission circuit 110*a* corresponding to any one channel is connected to one transducer element 30.

The interface circuit 11 is configured to communicate with the controlling circuit 160. For example, the interface circuit 11 is configured to receive various types of information and various types of data transmitted thereto from the controlling circuit 160.

For example, the interface circuit 11 is configured to receive a waveform signal transmitted thereto from the controlling circuit 160. The waveform signal is a signal of the transmission waveform (a signal indicating the transmission waveform) of the ultrasound wave transmitted from the transducer element 30 of the ultrasound probe 101. The waveform signal is input to the apparatus main body 100 by the user via the input interface 102. Further, the controlling circuit 160 is configured to transmit the input waveform signal to the interface circuit 11. After that, the interface circuit 11 is configured to store the received waveform signal into the waveform signal memory 12. In this situation, the waveform signal transmitted from the controlling circuit 160 is a signal in a digital format.

Further, the interface circuit 11 is configured to receive a generation instruction transmitted thereto from the controlling circuit 160. The generation instruction is an instruction to cause the DDS circuit 13 to generate a prescribed waveform signal. The generation instruction is input to the apparatus main body 100 by the user via the input interface 102. Further, the controlling circuit 160 is configured to transmit the input generation instruction to the interface circuit 11. After that, the interface circuit 11 is configured to transmit the received generation instruction to the DDS circuit 13.

Further, the interface circuit 11 is configured to receive an apodization mathematical function (hereinafter, simply "apodization function") transmitted thereto from the controlling circuit 160. The apodization function may be referred to as an aperture function or a transmission aperture function. The apodization function is a function set with a weight corresponding to each of different positions of the transducer element 30. For example, on the basis of an instruction from the user input via the input interface 102, the controlling circuit 160 is configured to generate the apodization function. After that, the controlling circuit 160 is configured to transmit the apodization function to the interface circuit 11. The interface circuit 11 is configured to store the received apodization function into the apodization register 14.

Further, the interface circuit 11 is configured to receive maximum amplitude (full scale) transmitted thereto from the controlling circuit 160. The maximum amplitude is a maximum amplitude level used in common among all the channels and is used at the time of amplifying the waveform signal. For example, the controlling circuit 160 is configured to transmit the maximum amplitude corresponding to the type of the ultrasound probe 101 connected to the apparatus main body 100, to the interface circuit 11. The interface circuit 11 is configured to store the receive maximum amplitude to the gain register 15.

Further, the interface circuit 11 is configured to receive a transmission delay time period (a transmission delay amount) transmitted thereto from the controlling circuit 160. The transmission delay time period is a delay time period with respect to the corresponding one of the channels, for example, the corresponding one of the transducer elements 30. For example, the controlling circuit 160 is configured to transmit the transmission delay time period to the interface circuit 11. The interface circuit 11 is configured to store the received transmission delay time period into the delay register 16.

Upon receipt of the generation instruction, the DDS circuit 13 is configured to generate the prescribed waveform signal according to the received generation instruction. The waveform signal is a signal in a digital format. Further, the DDS circuit 13 is configured to transmit the generated waveform signal to the waveform signal generating circuit 17.

The waveform signal generating circuit 17 is configured to generate a waveform signal having an arbitrary waveform. For example, the waveform signal generating circuit 17 is configured to generate the waveform signal having the arbitrary waveform on the basis of the waveform signal stored in the waveform signal memory 12. Alternatively, the waveform signal generating circuit 17 may generate the waveform signal having the arbitrary waveform, on the basis of a waveform signal automatically generated by the DDS circuit 13.

The following will describe an example of the process performed by the waveform signal generating circuit 17 to generate the waveform signal, on the basis of either the waveform signal stored in the waveform signal memory 12 or the waveform signal generated by the DDS circuit 13. For example, the waveform signal generating circuit 17 obtains, from among the waveform signals stored in the waveform signal memory 12, a waveform signal corresponding to an imaging mode input by the user via the input interface 102, the type of the ultrasound probe 101, or the like. Alternatively, the waveform signal generating circuit 17 may obtain the waveform signal transmitted thereto from the DDS circuit 13. After that, the waveform signal generating circuit 17 obtains the apodization function stored in the apodization register 14. Further, the waveform signal generating circuit 17 obtains the maximum amplitude stored in the gain register 15. In addition, the waveform signal generating circuit 17 obtains the transmission delay time period stored in the delay register 16.

After that, by using the apodization function, the waveform signal generating circuit 17 applies the weight corresponding to the transducer element 30, to the waveform signal. For example, to the waveform signal to be transmitted to the transducer element 30 of the one of the channels corresponding to the waveform signal generating circuit 17 among a plurality of transducer elements at the transmission aperture of the ultrasound probe 101, the waveform signal generating circuit 17 applies the weight corresponding to the transducer element 30 and being indicated by the apodization function.

After that, the waveform signal generating circuit 17 newly generates a waveform signal, by amplifying the weight-applied waveform signal so that the maximum amplitude of the weight-applied waveform signal is equal to the already-obtained maximum amplitude.

After that, the waveform signal generating circuit 17 applies the transmission delay time period to the newly-generated waveform signal. For example, the waveform signal generating circuit 17 transmits the newly-generated waveform signal to the controlling circuits 18 and 19, by delaying the transmission by the transmission delay time period from the timing of rising or falling of the pulse of a transmission trigger transmitted from the controlling circuit 160. Accordingly, the controlling circuits 18 and 19 receive mutually the same waveform signal. More specifically, the waveform signal generating circuit 17 transmits the newly-generated waveform signal to a decoder 18a and a switching element controlling circuit 18c (explained later) of the controlling circuit (controlling circuitry) 18 and to a decoder 19a and a switching element controlling circuit 19c (explained later) of the controlling circuit (controlling circuitry) 19.

In this situation, the waveform signal that was newly generated by the waveform signal generating circuit 17 exhibits the waveform of the ultrasound wave to be output from the transducer element 30.

Upon receipt of the waveform signal, the controlling circuit 18 controls, on the basis of the received waveform signal, a plurality of switching elements 22a and a switching element 23 (explained later) so that the waveform (the transmission waveform) of the ultrasound wave transmitted from the transducer element 30 is the waveform indicated by the waveform signal. Similarly, upon receipt of the waveform signal, the controlling circuit 19 controls, on the basis of the received waveform signal, a plurality of switching elements 26a and a switching element 27 (explained later) so that the transmission waveform of the ultrasound wave transmitted from the transducer element 30 is the waveform indicated by the waveform signal.

The controlling circuit 18 includes the decoder 18a, a switching element controlling circuit 18b, and the switching element controlling circuit 18c. The decoder 18a is connected to the switching element controlling circuit 18b. The controlling circuit 19 includes the decoder 19a, a switching element controlling circuit 19b, and the switching element controlling circuit 19c. The decoder 19a is connected to the switching element controlling circuit 19b. The controlling circuits 18 and 19 are realized by using one or more processors. The controlling circuits 18 and 19 will be explained later.

The power source line 20 is a wiring connected to a power source HVP with a positive electrode. The power source line 20 has the constant current circuit group 21 connected thereto. The power source HVP is a single power source.

The constant current circuit group 21 includes a plurality of constant current circuits 21a of which the quantity is equal to n (an integer of 2 or larger). For example, the n constant current circuits 21a are identical to one another. The n constant current circuits 21a are provided so as to be electrically positioned between the power source line 20 and the transducer element 30. The n constant current circuits 21a are connected in parallel to the power source line 20. Further, the n constant current circuits 21a are connected in parallel to the transducer element 30 via the switching element group 22 and the switching element 23. The constant current circuit group 21 has the switching element group 22 connected thereto.

In the present embodiment, for example, to cause a current of 1000 mA at a maximum to flow to the transducer element 30, the transmission circuit 110a includes, with respect to each of the channels, 100 constant current circuits 21a each configured to cause a constant current of 10 mA to flow. In another example, to cause a current of 2048 mA at a maximum to flow to the transducer element 30, the transmission circuit 110a includes, with respect to each of the channels, 128 constant current circuits 21a each configured to cause a constant current of 16 mA to flow. Possible examples of the quantity of the constant current circuits 21a included in the transmission circuit 110a in correspondence with each of the channels and the current value of the constant current caused to flow by each of the constant current circuits 21a are not limited to the examples presented above.

The switching element group 22 includes the switching elements 22a of which the quantity is equal to n. For example, the switching elements 22a are each realized by using a P-channel-type Metal-Oxide-Semiconductor Field Effect Transistor (MOSFET). Possible embodiments of the switching elements 22a are not limited to this example and may be realized by using other types of switching elements such as an N-channel-type MOSFET, a bipolar transistor, an insulated gate bipolar transistor, and/or the like. In the following sections, an example will be explained in which the switching elements 22a are each realized by using a P-channel-type MOSFET.

As illustrated in FIG. 2, each of the n switching elements 22a is provided so as to be electrically positioned between a corresponding one of the n constant current circuits 21a and the transducer element 30. The source of each of the n switching elements 22a is connected to a different one of the n constant current circuits 21a. Further, the drain of each of the n switching elements 22a is connected to the transducer element 30 via the switching element 23. More specifically, the drains of the n switching elements 22a are connected to the transducer element 30 by a single wiring (line) 28 via the switching element 23. Further, to the gate of each of the n switching elements 22a, the switching element controlling circuit 18b of the controlling circuit 18 is connected.

Under control of the switching element controlling circuit 18b, each of the switching elements 22a is configured to set the electrical connection state between the constant current circuit 21a connected to the switching element 22a and the transducer element 30 so as to be in one selected from between a first state and a second state. The electrical connection state between the constant current circuit 21a and the transducer element 30 may simply be referred to as a "connection state". The first state is a state in which the constant current circuit 21a is electrically connected to the transducer element 30. The second state is a state in which the connection between the constant current circuit 21a and the transducer element 30 is electrically blocked.

For example, when the voltage applied to the gate is negative (minus) voltage with respect to the source, the switching element 22a is in a conductive state. In that situation, the switching element 22a sets the connection state to be in the first state. In another example, when the voltage applied to the gate is positive (plus) voltage with respect to the source, the switching element 22a is in a non-conductive state. In that situation, the switching element 22a sets the connection state to be in the second state.

Accordingly, a current totaling the constant currents flowing in the switching elements 22a that are in the conductive state (i.e., the switching elements 22a that each set the connection state to be in the first state) among the n switching elements 22a flows to the transducer element 30 via the switching element 23.

The source of the switching element 23 is connected to the drain of each of the n switching elements 22a. Further, the gate of the switching element 23 is connected to the switching element controlling circuit 18c.

Further, the drain of the switching element 23 is connected to the transducer element 30 via the wiring 28. More specifically, of two electrodes of the transducer element 30, namely a first electrode 30a and a second electrode 30b, the drain is connected to the first electrode 30a. The second electrode 30b is grounded.

For example, the switching element 23 is realized by using a P-channel-type MOSFET.

Under control of the switching element controlling circuit 18c, the switching element 23 is configured to switch between the conductive state and the non-conductive state. For example, when the voltage applied to the gate is negative voltage with respect to the source, the switching element 23 is in the conductive state. On the contrary, when the voltage applied to the gate is positive voltage with respect to the source, the switching element 23 is in the non-conductive state.

Accordingly, while the switching element 23 is in the conductive state, a current totaling the constant currents flowing in the switching elements 22a that each set the connection state to be in the first state flows to the transducer element 30 via the switching element 23.

On the contrary, when the switching element 23 is in the non-conductive state, the currents from the constant current circuits 21a do not flow to the transducer element 30. Accordingly, when the switching element 23 is in the non-conductive state, it is possible to suppress leakage current from the constant current circuits 21a.

The power source line 24 is a wiring connected to a power source HVN with a negative electrode. The power source line 24 has the constant current circuit group 25 connected thereto. The power source HVN is a single power source.

The constant current circuit group 25 includes constant current circuits 25a of which the quantity is equal to n. Alternatively, while being two or more, the quantity of the constant current circuits 25a may be other than n. For example, the n constant current circuits 25a are identical to one another. The n constant current circuits 25a are provided so as to be electrically positioned between the power source line 24 and the transducer element 30. The n constant current circuits 25a are connected in parallel to the power source line 24. Further, the n constant current circuits 25a are connected in parallel to the transducer element 30 via the switching element group 26 and the switching element 27. The constant current circuit group 25 has the switching element group 26 connected thereto.

In the present embodiment, for example, to cause a current of −1000 mA at a minimum to flow to the transducer element 30, the transmission circuit 110a includes, with respect to each of the channels, 100 constant current circuits 25a each configured to cause a constant current of −10 mA to flow. In another example, to cause a current of −2048 mA at a minimum to flow to the transducer element 30, the transmission circuit 110a includes, with respect to each of the channels, 128 constant current circuits 25a each configured to cause a constant current of −16 mA to flow. Possible examples of the quantity of the constant current circuits 25a included in the transmission circuit 110a in correspondence with each of the channels and the current value of the constant current caused to flow by each of the constant current circuits 25a are not limited to the examples presented above.

The switching element group 26 includes the switching elements 26a of which the quantity is equal to n. For example, the switching elements 26a are each realized by an N-channel-type MOSFET. Possible embodiments of the switching elements 26a are not limited to this example and may be realized by using other types of switching elements such as a P-channel-type MOSFET, a bipolar transistor, an insulated gate bipolar transistor, and/or the like. In the following sections, an example will be explained in which the switching elements 26a are each realized by using an N-channel-type MOSFET.

As illustrated in FIG. 2, each of the n switching elements 26a is provided so as to be electrically positioned between a corresponding one of the n constant current circuits 25a and the transducer element 30. The source of each of the n switching elements 26a is connected to a different one of the n constant current circuits 25a. Further, the drain of each of the n switching elements 26a is connected to the transducer element 30 via the switching element 27. More specifically, the drains of the n switching elements 26a are connected to the transducer element 30 by the single wiring 28 via the switching element 27. Further, to the gate of each of the n switching elements 26a, the switching element controlling circuit 19b of the controlling circuit 19 is connected.

Under control of the switching element controlling circuit 19b, each of the switching elements 26a is configured to set the electrical connection state between the constant current circuit 25a connected to the switching element 26a and the transducer element 30 so as to be in one selected from between a first state and a second state. The electrical connection state between the constant current circuit 25a and the transducer element 30 may simply be referred to as a "connection state", similarly to the electrical connection state between the constant current circuit 21a and the transducer element 30. The first state in the present situation is a state in which the constant current circuit 25a is electrically connected to the transducer element 30. The second state is a state in which the connection between the constant current circuit 25a and the transducer element 30 is electrically blocked.

For example, when the voltage applied to the gate is positive (plus) voltage with respect to the source, the switching element 26a is in a conductive state. In that situation, the switching element 26a sets the connection state to be in the first state. In another example, when the voltage applied to the gate is negative (minus) voltage with respect to the source, the switching element 26a is in a non-conductive state. In that situation, the switching element 26a sets the connection state to be in the second state.

Accordingly, a current totaling the constant currents flowing in the switching elements 26a that are in the conductive state (i.e., the switching elements 26a that each set the connection state to be in the first state) among the n switching elements 26a flows to the transducer element 30 via the switching element 27.

The source of the switching element 27 is connected to the drain of each of the n switching elements 26a. Further, the gate of the switching element 27 is connected to the switching element controlling circuit 19c.

Further, the drain of the switching element 27 is connected to the transducer element 30 via the wiring 28. More specifically, the drain of the switching element 27 is connected to the first electrode 30a included in the transducer element 30.

For example, the switching element 27 is realized by using an N-channel-type MOSFET.

Under control of the switching element controlling circuit 19c, the switching element 27 is configured to switch between the conductive state and the non-conductive state. For example, when the voltage applied to the gate is positive (plus) voltage with respect to the source, the switching element 27 is in the conductive state. On the contrary, when the voltage applied to the gate is negative (minus) voltage with respect to the source, the switching element 27 is in the non-conductive state.

Accordingly, while the switching element 27 is in the conductive state, a current totaling the constant currents flowing in the switching elements 26a that each set the connection state to be in the first state flows to the transducer element 30.

On the contrary, when the switching element 27 is in the non-conductive state, the current totaling the constant currents flowing in the switching elements 26a that each set the connection state to be in the first state does not flow to the transducer element 30.

Figure 3:
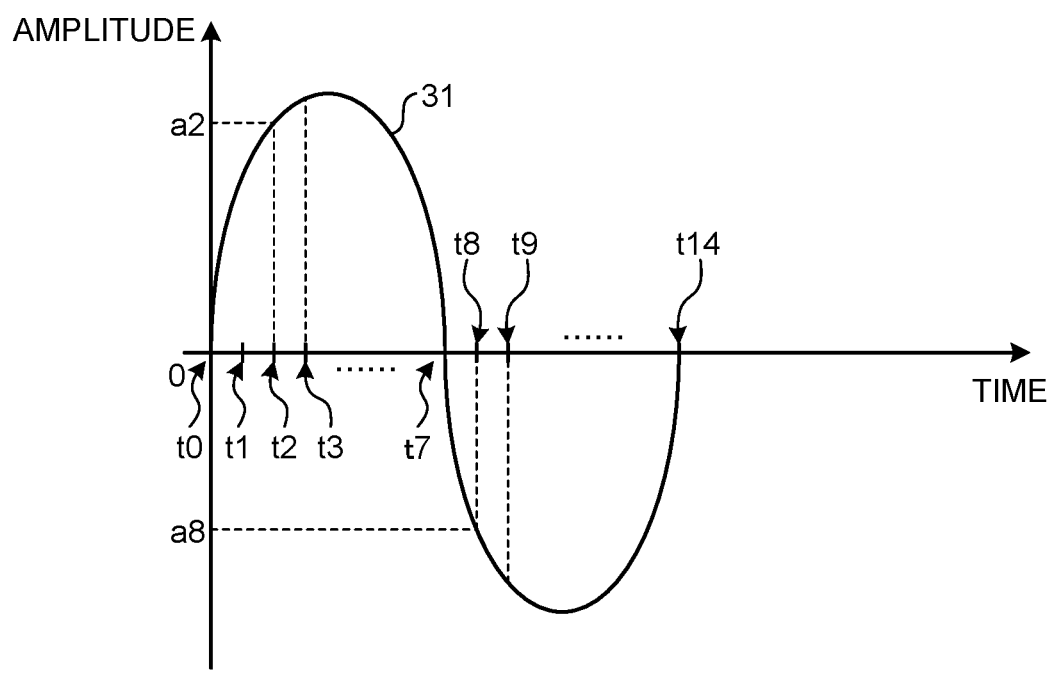
FIG. 3 is a chart for explaining an example of an operation performed by the transmission circuit according to the first embodiment.

Next, an example of an operation performed by the transmission circuit 110a will be explained. FIG. 3 is a chart for explaining the example of the operation performed by the transmission circuit 110a according to the first embodiment. As explained above the waveform signal received by the controlling circuit 18 and the waveform signal received by the controlling circuit 19 are mutually the same waveform signal. In the following sections, an example will be explained in which the controlling circuits 18 and 19 perform processes by using mutually the same waveform signal 31 illustrated in FIG. 3. For example, a situation will be explained in which, on the basis of the waveform signal 31 having a transmission waveform illustrated in FIG. 3, the controlling circuits 18 and 19 control the n switching elements 22a, the switching element 23, the n switching elements 26a, and the switching element 27.

More specifically, on the basis of the waveform signal 31, the controlling circuit 18 causes each of the n switching elements 22a to set the connection state between the corresponding one of the n constant current circuits 21a and the transducer element 30 to be in one of the first and the second states. For example, the controlling circuit 18 causes the connection state between each of the n constant current circuits 21a and the transducer element 30 to be in one of the first and the second states, so that an ultrasound wave having the waveform indicated by the waveform signal 31 is transmitted from the transducer element 30 in the cycle of the waveform indicated by the waveform signal 31.

Similarly, on the basis of the waveform signal 31, the controlling circuit 19 causes each of the n switching elements 26a to set the connection state between the corresponding one of the n constant current circuits 25a and the transducer element 30 to be in one of the first and the second states. For example, the controlling circuit 19 causes the connection state between each of the n constant current circuits 25a and the transducer element 30 to be in one of the first and the second states, so that an ultrasound wave having the waveform indicated by the waveform signal 31 is transmitted from the transducer element 30 in the cycle of the waveform indicated by the waveform signal 31. In the following sections, specific examples of the processes performed by the controlling circuits 18 and 19 will be explained.

The transmission waveform in FIG. 3 is illustrated in a graph of which the horizontal axis expresses time, whereas the vertical axis expresses amplitude. Every cycle indicated by a system clock of the ultrasound diagnosis apparatus 1, the decoders 18a and 19a and the switching element controlling circuits 18c and 19c judge which one of the following values the amplitude (the amplitude value) indicated by the waveform signal 31 has: a positive value, a negative value, and "0" which is a value that is neither positive or negative.

For example, at each of the times t0 to t14 indicated in FIG. 3, the decoders 18a and 19a and the switching element controlling circuits 18c and 19c judge which one of the values (a positive value, a negative value, and "0") the amplitude indicated by the waveform signal 31 has. The timing of the times t0 to t14 is the timing of each cycle indicated by the system clock.

Upon determination that the amplitude indicated by the waveform signal 31 is a positive value, the decoder 18a performs the following process: For example, the decoder 18a identifies the quantity of the switching elements 22a that are in the conductive state when a current having the current value corresponding to the amplitude indicated by the waveform signal 31 flows to the transducer element 30. In other words, the decoder 18a identifies the quantity of the switching elements 22a that each set the connection state to be in the first state. Further, the decoder 18a outputs a waveform code indicating the identified quantity of the switching elements 22a, to the switching element controlling circuit 18b.

For example, as illustrated in FIG. 3, at the time t2, the decoder 18a determines the amplitude "a2" indicated by the waveform signal 31 is a positive value. Upon the determination, the decoder 18a identifies the quantity of the switching elements 22a in the conductive state when a current having the current value corresponding to the amplitude "a2" flows to the transducer element 30. For example, the decoder 18a includes a memory storing therein a table that has registered current values of the current flowing to the transducer element 30 so as to be each kept in correspondence with a different one of a plurality of amplitude values. Further, by referring to the table, the decoder 18a obtains the current value corresponding to the amplitude "a2". After that, the decoder 18a calculates the quantity of the switching elements 22a in the conductive state on the basis of the obtained current value, the current value of the constant current caused to flow by each constant current circuit 21a, resistance values between the constant current circuits 21a and the transducer element 30, and the like. As described herein, the decoder 18a has identified the quantity of the switching elements 22a in the conductive state.

Possible methods for identifying the quantity of the switching elements 22a in the conductive state are not limited to the method described above. For instance, the decoder 18a may include a memory storing therein a table that has registered quantities of the switching elements 22a in the conductive state so as to be each kept in correspondence with a different one of a plurality of amplitude values. Further, by referring to the table, the decoder 18a may identify the quantity of the switching elements 22a in the conductive state corresponding to the amplitude "a2". After that, the decoder 18a outputs the waveform code indicating the identified quantity to the switching element controlling circuit 18b. In the following sections, the identified quantity will be referred to as "m (being an integer of 0 or larger)".

Figure 4:
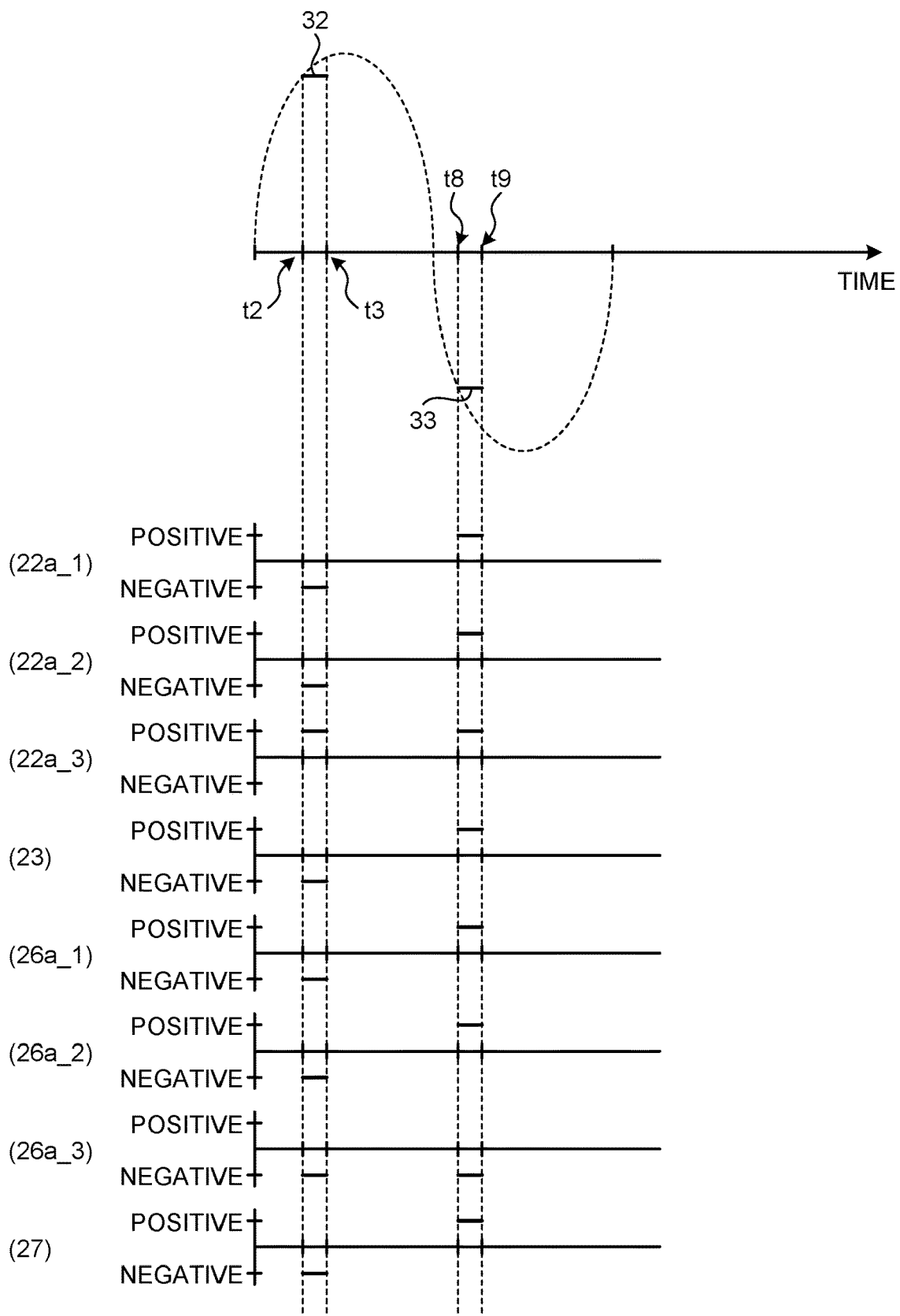
FIG. 4 is a timing chart illustrating an example of an operation performed by the transmission circuit according to the first embodiment.

FIG. 4 is a timing chart illustrating an example of an operation performed by the transmission circuit 110a according to the first embodiment. FIG. 4 illustrates an example in which "n" is equal to "3". In the example in FIG. 4, "m" is equal to "2" between the times t2 and t3. Further, in FIG. 4, to distinguish among the n (three) switching elements 22a, the reference symbols "22a_1" to "22a_3" are assigned to the n switching elements 22a. Further, for the same reason, to distinguish among the n switching elements 26a, the reference symbols "26a_1" to "26a_3" are assigned to the n switching elements 26a.

Further, upon receipt of the waveform code, the switching element controlling circuit 18b controls the n switching elements 22a_1 to 22a_3 on the basis of the received waveform code. For example, as illustrated in FIG. 4, between the times t2 and t3, the switching element controlling circuit 18b applies negative voltage with respect to the source, to the gates of m (two) switching elements 22a_1 and 22a_2, the value of m being indicated by the waveform code. Further, as illustrated in FIG. 4, between the times t2 and t3, the switching element controlling circuit 18b applies positive voltage with respect to the source, to the gate of "n-m" (one) switching element 22a_3.

Further, upon determination that the amplitude indicated by the waveform signal 31 is a positive value, the switching element controlling circuit 18c applies negative voltage with respect to the source, to the gate of the switching element 23. In other words, while the amplitude indicated by the waveform signal 31 is a positive value, the switching element controlling circuit 18c keeps applying the negative voltage with respect to the source, to the gate of the switching element 23. Accordingly, as illustrated in FIG. 4, between the times t2 and t3, the negative voltage with respect to the source is applied to the gate of the switching element 23.

In this situation, upon determination that the amplitude indicated by the waveform signal 31 is a positive value, the decoder 19a identifies the quantity of the switching elements 26a that each set the connection state to be in the first state as "0". After that, the decoder 19a outputs a waveform code indicating the identified quantity "0" to the switching element controlling circuit 19b. Further, the switching element controlling circuit 19b applies negative voltage with respect to the source, to the gates of "n-0" (where 0 is the value indicated by the waveform code) switching elements 26a_1 to 26a_3. In other words, while the amplitude indicated by the waveform signal 31 is a positive value, the switching element controlling circuit 19b keeps applying the negative voltage with respect to the source, to the gates of the n switching elements 26a_1 to 26a_3. Accordingly, as illustrated in FIG. 4, the negative voltage with respect to the source is applied to the gates of the n switching elements 26a_1 to 26a_3 between the times t2 and t3.

Further, upon determination that the amplitude indicated by the waveform signal 31 is a positive value, the switching element controlling circuit 19c applies negative voltage with respect to the source, to the gate of the switching element 27. In other words, while the amplitude indicated by the waveform signal 31 is a positive value, the switching element controlling circuit 19c keeps applying the negative voltage with respect to the source, to the gate of the switching element 27. Accordingly, as illustrated in FIG. 4, the negative voltage with respect to the source is applied to the gate of the switching element 27 between the times t2 and t3.

As a result, between the times t2 and t3, a current totaling the constant currents flowing from the two constant current circuits 21a flows to the transducer element 30. Further, a waveform 32 between the times t2 and t3 of the ultrasound wave transmitted from the transducer element 30 illustrated in FIG. 4 is substantially the same as the waveform between the times t2 and t3 of the waveform signal 31 illustrated in FIG. 3.

As another example, upon determination that the amplitude indicated by the waveform signal 31 has the value "0", the decoder 18a identifies the quantity of the switching elements 22a that each set the connection state to be in the first state as "0". Further, the decoder 18a outputs a waveform code indicating the identified quantity "0" to the switching element controlling circuit 18b. Upon receipt of the waveform code indicating the quantity "0", the switching element controlling circuit 18b applies positive voltage with respect to the source, to the gates of "n-0 (where 0 is the value indicated by the waveform code)" switching elements 22a_1 to 22a_3, on the basis of the waveform code.

Further, upon determination that the amplitude indicated by the waveform signal 31 has the "0" value, the switching element controlling circuit 18c applies positive voltage with respect to the source, to the gate of the switching element 23.

Similarly, upon determination that the amplitude indicated by the waveform signal 31 has the value "0", the decoder 19a identifies the quantity of the switching elements 26a that each set the connection state to be in the first state as "0". Further, the decoder 19a outputs a waveform code indicating the identified quantity "0" to the switching element controlling circuit 19b. Upon receipt of the waveform code indicating the quantity "0", the switching element controlling circuit 19b applies negative voltage with respect to the source, to the gates of the "n-0 (where 0 is the value indicated by the waveform code)" switching elements 26a_1 to 26a_3, on the basis of the waveform code.

Further, upon determination that the amplitude indicated by the waveform signal 31 has the "0" value, the switching element controlling circuit 19c applies negative voltage with respect to the source, to the gate of the switching element 27.

As yet another example, upon determination that the amplitude indicated by the waveform signal 31 is a negative value, the decoder 19a performs the following process: For example, the decoder 19a identifies the quantity of the switching elements 26a that are in the conductive state when a current having the current value corresponding to the amplitude indicated by the waveform signal 31 flows to the transducer element 30. In other words, the decoder 19a identifies the quantity of the switching elements 26a that each set the connection state to be in the first state.

After that, the decoder 19a outputs a waveform code indicating the identified quantity of the switching elements 26a, to the switching element controlling circuit 19b. For example, the decoder 19a identifies the quantity of the switching elements 26a in the conductive state, by using the same method as the method used by the decoder 18a for identifying the quantity of the switching elements 22a in the conductive state.

For example, as illustrated in FIG. 3, at the time t8, the decoder 19a determines that the amplitude "a8" indicated by the waveform signal 31 is a negative value. Upon the determination, the decoder 19a identifies the quantity of the switching elements 26a in the conductive state when a current having the current value corresponding to the amplitude "a8" flows to the transducer element 30. In the following sections, the identified quantity will be referred to as "q (being an integer of 0 or larger)".

In this situation, with reference back to FIG. 4, "q" is equal to "2" between the times t8 and t9. Further, upon receipt of the waveform code, the switching element controlling circuit 19b controls the n switching elements 26a_1 to 26a_3 on the basis of the received waveform code. For example, as illustrated in FIG. 4, between the times t8 and t9, the switching element controlling circuit 19b applies positive voltage with respect to the source, to the gates of q (two) switching elements 26a_1 and 26a_2, the value of q being indicated by the waveform code. Further, as illustrated in FIG. 4, between the times t8 and t9, the switching element controlling circuit 19b applies negative voltage with respect to the source, to the gate of "n-q" (one) switching element 26a_3.

Further, upon determination that the amplitude indicated by the waveform signal 31 is a negative value, the switching element controlling circuit 19c applies positive voltage with respect to the source, to the gate of the switching element 27. In other words, while the amplitude indicated by the waveform signal 31 is a negative value, the switching element controlling circuit 19c keeps applying the positive voltage with respect to the source, to the gate of the switching element 27. Accordingly, as illustrated in FIG. 4, between the times t8 and t9, the positive voltage with respect to the source is applied to the gate of the switching element 27.

In this situation, upon determination that the amplitude indicated by the waveform signal 31 is a negative value, the decoder 18a identifies the quantity of the switching elements 22a that each set the connection state to be in the first state as "0". After that, the decoder 18a outputs a waveform code indicating the identified quantity "0" to the switching element controlling circuit 18b. Further, the switching element controlling circuit 18b applies positive voltage with respect to the source, to the gates of the "n-0 (where 0 is the value indicated by the waveform code)" switching elements 22a_1 to 22a_3. In other words, while the amplitude indicated by the waveform signal 31 is a negative value, the switching element controlling circuit 18b keeps applying the positive voltage with respect to the source, to the gates of the n switching elements 22a_1 to 22a_3. Accordingly, as illustrated in FIG. 4, between the times t8 and t9, the positive voltage with respect to the source is applied to the gates of the n switching elements 22a_1 to 22a_3.

Further, upon determination that the amplitude indicated by the waveform signal 31 is a negative value, the switching element controlling circuit 18c applies positive voltage with respect to the source, to the gate of the switching element 23. In other words, while the amplitude indicated by the waveform signal 31 is a negative value, the switching element controlling circuit 18c keeps applying the positive voltage with respect to the source, to the gate of the switching element 23. Accordingly, as illustrated in FIG. 4, between the times t8 and t9, the positive voltage with respect to the source is applied to the gate of the switching element 23.

As a result, between the times t8 and t9, a current totaling the constant currents flowing from the two constant current circuits 25a flows to the transducer element 30. Further, as illustrated in FIG. 4, a waveform 33 between the times t8 and t9 is substantially the same as the waveform between the times t8 and t9 of the waveform signal 31 illustrated in FIG. 3.

By performing the operation (the process) described above in every cycle of the system clock, the ultrasound diagnosis apparatus 1 according to the first embodiment is able to cause the waveform of the ultrasound wave transmitted from the transducer element 30 to be the same as the waveform indicated by the waveform signal 31.

The ultrasound diagnosis apparatus 1 and the transmission circuit 110a according to the first embodiment have thus been explained. In the first embodiment, the transmission circuit 110a causes the transducer element 30 to transmit the ultrasound wave having the arbitrary waveform, without using a linear amplifier having large power consumption such as that included in the ultrasound diagnosis apparatus according to the comparison example. Consequently, by using the ultrasound diagnosis apparatus 1 and the transmission circuit 110a according to the first embodiment, it is possible to suppress the power consumption. Further, by using the transmission circuit 110a according to the first embodiment, it is possible to cause the transducer element 30 to transmit the ultrasound wave having the arbitrary waveform while suppressing the power consumption. In addition, by using the ultrasound diagnosis apparatus 1 according to the first embodiment, it is possible to cause the ultrasound wave having the arbitrary waveform to be transmitted while suppressing the power consumption.

Furthermore, the transmission circuit 110a according to the first embodiment does not employ a linear amplifier such as that included in the ultrasound diagnosis apparatus according to the comparison example. For this reason, the transmission circuit 110a does not employ a DAC circuit such as that employed in the comparison example. In other words, the transmission circuit 110a causes the transducer element 30 to transmit the ultrasound wave having the arbitrary waveform, without using a DAC circuit that is large in size and has a high cost. Accordingly, by using the ultrasound diagnosis apparatus 1 and the transmission circuit 110a according to the first embodiment, it is possible to suppress the size and the cost. Further, by using the transmission circuit 110a according to the first embodiment, it is possible to cause the transducer element 30 to transmit the ultrasound wave having the arbitrary waveform, while suppressing the size and the cost. In addition, by using the ultrasound diagnosis apparatus 1 according to the first embodiment, it is possible to cause the ultrasound wave having the arbitrary waveform to be transmitted, while suppressing the size and the cost.

Moreover, because the size and the cost of the transmission circuit 110a are suppressed, it is possible to apply the transmission circuit 110a, not only to high-end ultrasound diagnosis apparatuses, but also to medium-range (medium class) ultrasound diagnosis apparatuses. Accordingly, the medium-range ultrasound diagnosis apparatuses also become able to cause an ultrasound wave having an arbitrary waveform to be transmitted. Consequently, it is also possible to enhance capabilities of the medium-range ultrasound diagnosis apparatuses.

Second Embodiment

Next, the ultrasound diagnosis apparatus 1 according to a second embodiment will be explained. In the second embodiment, it is possible to further suppress the size and the cost of the transmission circuit compared to the first embodiment, by using constant current circuits having flows of constant currents smaller than those of the constant current circuits 21a and 25a according to the first embodiment. In the description of the second embodiment, differences from the first embodiment will primarily be explained, and the explanations of some of the constituent elements that are the same as those in the first embodiment may be omitted. For example, in the description of the second embodiment, some of the constituent elements that are the same as those in the first embodiment may be referred to by using the same reference characters, and the explanations thereof may be omitted.

Figure 5:
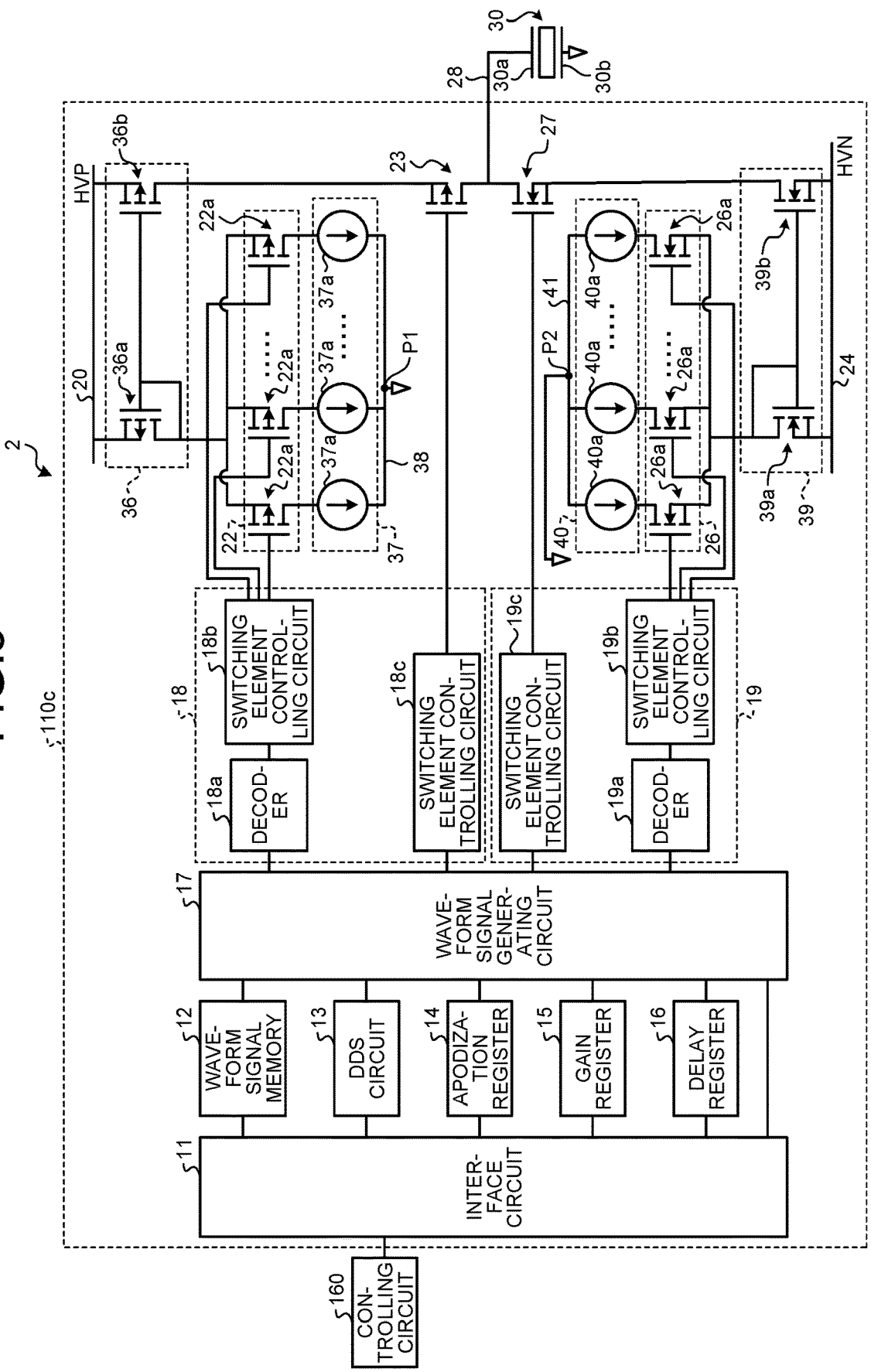
FIG. 5 is a diagram illustrating an exemplary configuration corresponding to any one of the channels in a transmission circuit according to a second embodiment.

FIG. 5 is a diagram illustrating an exemplary configuration corresponding to any one of the channels in a transmission circuit 110c according to the second embodiment. An ultrasound diagnosis apparatus 2 according to the second embodiment is different from the ultrasound diagnosis apparatus 1 according to the first embodiment for including the transmission circuit 110c illustrated in FIG. 5, in place of the transmission circuit 110a. Further, the transmission circuit 110c is different from the transmission circuit 110a according to the first embodiment for including constant current circuit groups 37 and 40, in place of the constant current circuit groups 21 and 25. Also, the transmission circuit 110c is different from the transmission circuit 110a for including current mirror circuits 36 and 39 and wirings 38 and 41.

As illustrated in FIG. 5, to the power source line 20, the current mirror circuit 36 is connected. The current mirror circuit 36 includes two transistors 36a and 36b.

Each of the two transistors 36a and 36b is realized by using a P-channel-type MOSFET, for example. Possible embodiments of the transistors 36a and 36b are not limited to this example and may be realized by using other types of transistors such as an N-channel-type MOSFET, a bipolar transistor, an insulated gate bipolar transistor, and/or the like. In the following sections, an example will be explained in which the transistors 36a and 36b are each realized by using a P-channel-type MOSFET. The drains of the transistors 36a and 36b are each an example of the drain (outflow) terminal. The gates of the transistors 36a and 36b are each an example of the controlling terminal. The sources of the transistors 36a and 36b are each an example of a source (inflow) terminal.

The source of the transistor 36a and the source of the transistor 36b are connected to the power source line 20. Further, the gate of the transistor 36a is connected to the gate of the transistor 36b. In addition, the drain of the transistor 36a is connected to each of the n switching elements 22a. Furthermore, the drain of the transistor 36a is connected to each of n constant current circuits 37a (explained later) via a corresponding one of the n switching elements 22a. In other words, as illustrated in FIG. 5, the transistor 36a is provided so as to be electrically positioned between the power source line 20 and the n constant current circuits 37a. Further, the gate and the drain of the transistor 36a are connected to each other. The transistor 36a is an example of the first transistor.

The drain of the transistor 36b is connected to the source of the switching element 23. Further, as illustrated in FIG. 5, the drain of the transistor 36b is connected to the transducer element 30 via the switching element 23 and the wiring 28. In other words, as illustrated in FIG. 5, the transistor 36b is provided so as to be electrically positioned between the power source line 20 and the transducer element 30. The transistor 36b is an example of the second transistor.

In the second embodiment, when a current (a reference current) flows to the transistor 36a in the current mirror circuit 36, a current (an output current) having the same current value as that of the reference current flows to the transistor 36b. In other words, the output current flows to the transducer element 30 via the switching element 23.

The source of each of the n switching elements 22a is connected to the drain of the transistor 36a explained above. Further, the drain of each of the n switching elements 22a is connected to a different one of the n constant current circuits 37a (explained later). As illustrated in FIG. 5, each of the n switching elements 22a is provided so as to be electrically positioned between the corresponding one of the n constant current circuits 37a and the transistor 36a.

In the second embodiment, under control of the switching element controlling circuit 18b, each of the switching elements 22a is configured to set the electrical connection state between the constant current circuit 37a connected to the switching element 22a and the transistor 36a so as to be in one selected from between a first state and a second state. The electrical connection state between the constant current circuit 37a and the transistor 36a may simply be referred to as a "connection state". In the second embodiment, the first state is a state in which the constant current circuit 37a is electrically connected to the transistor 36a. The second state is a state in which the connection between the constant current circuit 37a and the transistor 36a is electrically blocked.

The constant current circuit group 37 is connected to the switching element group 22. More specifically, the constant current circuit group 37 includes the n constant current circuits 37a. For example, the n constant current circuits 37a are identical to one another. The n constant current circuits 37a are grounded via the one wiring 38. In other words, the n constant current circuits 37a are connected to a potential point P1 being provided on the wiring 38 and having specific potential.

As illustrated in FIG. 5, the n constant current circuits 37a are provided so as to be electrically positioned between the power source line 20 and the potential point P1. Further, the n constant current circuits 37a are connected in parallel to the power source line 20 via the switching element group 22 and the transistor 36a. Further, the n constant current circuits 37a are also connected in parallel to the potential point P1.

In the second embodiment, for example, it is possible to further suppress the size and the cost of the constant current circuits compared to the first embodiment, by ensuring that the current amplification factor of the transistors 36a and 36b included in the current mirror circuit 36 is larger than "1". In the following sections, the first embodiment will be compared with the second embodiment while using the situation where a current of 1000 mA at a maximum is caused to flow to the transducer element 30. For example, in the first embodiment, the transmission circuit 110a needs to include, with respect to each of the channels, 100 constant current circuits 21a to cause a constant current of 10 mA to flow. In contrast, in the second embodiment, in the situation where the current amplification factor of the transistors 36a and 36b is "10", it is sufficient when the transmission circuit 110c includes, with respect to each of the channels, 100 constant current circuits 37a to cause a constant current of 1 mA to flow or 10 constant current circuits 37a to cause a constant current of 10 mA to flow.

Let us discuss the example in which the transmission circuit 110c includes, with respect to each of the channels, 100 constant current circuits 37a to cause a constant current of 1 mA to flow. The smaller the constant current value is, the smaller is the size of the constant current circuit and the lower is the cost. Accordingly, the size of the constant current circuit 37a for causing the constant current of 1 mA to flow is smaller than the size of the constant current circuit 21a for causing a constant current of 10 mA to flow. Also, the cost of the constant current circuit 37a for causing the constant current of 1 mA to flow is lower than the cost of the constant current circuit 21a for causing a constant current of 10 mA to flow. Consequently, the size and the cost of the transmission circuit 110c are suppressed compared to the size and the cost of the transmission circuit 110a.

Next, let us discuss the other example in which the transmission circuit 110c includes, with respect to each of the channels, 10 constant current circuits 37a to cause a constant current of 10 mA to flow. In this situation, the size and the cost of each of the constant current circuits 21a included in the transmission circuit 110a are substantially the same as the size and the cost of each of the constant current circuits 37a included in the transmission circuit 110c. However, in contrast to the transmission circuit 110a including the 100 constant current circuits 21a, the transmission circuit 110c is sufficient by including only the 10 constant current circuits 37a. Accordingly, compared to the size and the cost of the transmission circuit 110a, the size and the cost of the transmission circuit 110c are suppressed.

Next, the controlling circuit 18 according to the second embodiment will be explained. In the first embodiment, the example was explained in which the controlling circuit 18 is configured to cause each of the n switching elements 22a to set the connection state to be in one of the first and the second states, on the basis of the waveform signal. Similarly to the first embodiment, in the second embodiment also, the controlling circuit 18 is configured to cause each of the n switching elements 22a to set the connection state to be in one of the first and the second states, on the basis of a waveform signal. Further, similarly to the first embodiment, in the second embodiment also, the controlling circuit 18 is configured to control the switching element 23 on the basis of the waveform signal.

Further, as illustrated in FIG. 5, to the power source line 24, the current mirror circuit 39 is connected. The current mirror circuit 39 includes two transistors 39a and 39b.

For example, the two transistors 39a and 39b are each realized by using a N-channel-type MOSFET. Possible embodiments of the transistors 39a and 39b are not limited to this example and may be realized by using other types of transistors such as a P-channel-type MOSFET, a bipolar transistor, an insulated gate bipolar transistor, and/or the like. In the following sections, however, an example will be explained in which the transistors 39a and 39b are each realized by using a N-channel-type MOSFET. The drains of the transistors 39a and 39b are each an example of the drain (outflow) terminal. The gates of the transistors 39a and 39b are each an example of the controlling terminal. The sources of the transistors 39a and 39b are each an example of a source (inflow) terminal.

The source of the transistor 39a and the source of the transistor 39b are connected to the power source line 24. The gate of the transistor 39a is connected to the gate of the transistor 39b. Further, the drain of the transistor 39a is connected to each of the n switching elements 26a. Also, the drain of the transistor 39a is connected to each of n constant current circuits 40a (explained later) via a corresponding one of the n switching elements 26a. In other words, as illustrated in FIG. 5, the transistor 39a is provided so as to be electrically positioned between the power source line 24 and the n constant current circuits 40a. Further, the gate and the drain of the transistor 39a are connected to each other. The transistor 39a is an example of the first transistor.

The drain of the transistor 39b is connected to the source of the switching element 27. Further, as illustrated in FIG. 5, the drain of the transistor 39b is connected to the transducer element 30 via the switching element 27 and the wiring 28. In other words, as illustrated in FIG. 5, the transistor 39b is provided so as to be electrically positioned between the power source line 24 and the transducer element 30. The transistor 39b is an example of the second transistor.

In the second embodiment, when a current (a reference current) flows to the transistor 39a in the current mirror circuit 39, a current (an output current) having the same current value as that of the reference current flows to the transistor 39b. In other words, the output current flows to the transducer element 30.

The source of each of the n switching elements 26a is connected to the drain of the transistor 39a described above. Further, the drain of each of the n switching elements 26a is connected to a different one of the n constant current circuits 40a (explained later). As illustrated in FIG. 5, each of the n switching elements 26a is provided so as to be electrically positioned between a corresponding one of the n constant current circuits 40a and the transistor 39a.

In the second embodiment, under the control of the switching element controlling circuit 19b, each of the switching elements 26a is configured to set the electrical connection state between the constant current circuit 40a connected to the switching element 26a and the transistor 39a so as to be in one selected from between a first state and a second state. The electrical connection state between the constant current circuit 40a and the transistor 39a may simply be referred to as a "connection state". In the second embodiment, the first state is a state in which the constant current circuit 40a is electrically connected to the transistor 39a. The second state is a state in which the connection between the constant current circuit 40a and the transistor 39a is electrically blocked.

The constant current circuit group 40 is connected to the switching element group 26. The constant current circuit group 40 includes the n constant current circuits 40a. For example, the n constant current circuits 40a are identical to one another. The n constant current circuits 40a are grounded via the single wiring 41. In other words, the n constant current circuits 40a are connected to a potential point P2 being provided on the wiring 41 and having specific potential.

As illustrated in FIG. 5, the n constant current circuits 40a are provided so as to be electrically positioned between the power source line 24 and the potential point P2. Further, the n constant current circuits 40a are connected in parallel to the power source line 24 via the switching element group 26 and the transistor 39a. In addition, the n constant current circuits 40a are also connected in parallel to the potential point P2.

In the second embodiment, for example, it is possible to further suppress the size and the cost of the constant current circuits compared to the first embodiment, by ensuring that the current amplification factor of the transistors 39a and 39b included in the current mirror circuit 39 is larger than "1". In the following sections, the first embodiment will be compared with the second embodiment while using the situation where a current of −1000 mA at a minimum is caused to flow to the transducer element 30. For example, in the first embodiment, the transmission circuit 110a needs to include, with respect to each of the channels, 100 constant current circuits 25a to cause a constant current of −10 mA to flow. In contrast, in the second embodiment, in the situation where the current amplification factor of the transistors 39a and 39b is "10", it is sufficient when the transmission circuit 110c includes, with respect to each of the channels, 10 constant current circuits 40a to cause a constant current of −10 mA to flow or 100 constant current circuits 40a to cause a constant current of −1 mA to flow.

Accordingly, the size and the cost of the transmission circuit 110c are suppressed compared to the size and the cost of the transmission circuit 110a.

Next, the controlling circuit 19 according to the second embodiment will be explained. In the first embodiment, the example was explained in which the controlling circuit 19 is configured to cause each of the n switching elements 26a to set the connection state to be in one of the first and the second states, on the basis of the waveform signal. Similarly to the first embodiment, in the second embodiment also, the controlling circuit 19 is configured to cause each of the n switching elements 26a to set the connection state to be in one of the first and the second states, on the basis of a waveform signal. Further, similarly to the first embodiment, in the second embodiment also, the controlling circuit 19 is configured to control the switching element 27 on the basis of the waveform signal.

The ultrasound diagnosis apparatus 2 according to the second embodiment has thus been explained. By using the ultrasound diagnosis apparatus 2, it is possible to suppress power consumption, similarly to the example of the ultrasound diagnosis apparatus 1.

Further, according to the second embodiment, it is possible to further suppress the size and the cost of the transmission circuit compared to the first embodiment. Consequently, according to the second embodiment, it is possible to further suppress the size and the cost of the ultrasound diagnosis apparatus, compared to the first embodiment.

Modification Examples

Next, various types of modification examples will be explained. For example, in the first embodiment, the n constant current circuits 21a are identical to one another, while the n constant current circuits 25a are identical to one another. Similarly, in the second embodiment, the n constant current circuits 37a are identical to one another, while the n constant current circuits 40a are identical to one another. However, the n constant current circuits 21a may include at least one constant current circuit that is different from the other constant current circuits. In other words, among the plurality of constant current values output from the plurality of constant current circuits 21a, at least one value may be different from the other values. The same applies to the n constant current circuits 25a, the n constant current circuits 37a, and the n constant current circuits 40a.

For instance, in the first embodiment, let us discuss an example in which the values of the current flowing to the transducer element 30 are determined to be three current values such as "10 mA", "20 mA", and "30 mA". In this situation, the transmission circuit 110a includes one constant current circuit 21a causing a constant current of 10 mA to flow and another constant current circuit 21a causing a constant current of 20 mA to flow, instead of including three constant current circuits 21a each causing a constant current of 10 mA to flow. In other words, the transmission circuit 110a includes two or more constant current circuits 21a of a combination that minimizes the size and the cost of the transmission circuit 110a, among various combinations of a plurality of constant current circuits 21a capable of causing a current having the determined plurality of current values to flow to the transducer element 30. For example, the quantity of the constant current circuits 21a included in the transmission circuit 110a is the smallest quantity among various quantities of the constant current circuits 21a capable of causing the waveform indicated by the waveform signal 31 to be output from the transducer element 30.

In this situation, in the first and the second embodiment, the controlling circuits 18 and 19 are configured to identify the switching elements that are in the conductive state, instead of identifying the quantity of the switching elements that are in the conductive state.

Further, in the first and the second embodiments, the example was explained in which the apparatus main body 100 includes the transmission circuit 110a. Alternatively, however, the ultrasound probe 101 may include the transmission circuit 110a. In another example, the ultrasound probe 101 may include a circuit having a part of the functions of the transmission circuit 110a. For example, when the ultrasound probe 101 is a 2D array probe or when the ultrasound diagnosis apparatus 1 or 2 is a tablet ultrasound diagnosis apparatus, the ultrasound probe 101 may include the transmission circuit 110a or a circuit having a part of the functions of the transmission circuit 110a.

Further, in the first embodiment, the example was explained in which the n constant current circuits 21a are connected in parallel to the power source line 20 and the transducer element 30. Further, the example was explained in which the n constant current circuits 25a are connected in parallel to the power source line 24 and the transducer element 30. Alternatively, it is also acceptable to connect n resistors having mutually-different resistance values in parallel to the power source line 20 and the transducer element 30, in place of the n constant current circuits 21a. In other words, each of the n resistors may be connected to a different one of the n switching elements 22a. Further, the controlling circuit 18 may be configured to control the resistance values by setting, in accordance with the waveform signal, the state of each of the n switching elements 22a to be in one of the conductive state and the non-conductive state.

Similarly, it is also acceptable to connect n resistors having mutually-different resistance values in parallel to the power source line 24 and the transducer element 30, in place of the n constant current circuits 25a. In other words, each of the n resistors may be connected to a different one of the n switching elements 26a. Further, the controlling circuit 19 may be configured to control the resistance values by setting, in accordance with the waveform signal, the state of each of the n switching elements 26a to be in one of the conductive state and the non-conductive state.

By controlling the resistance values in the manner described above, the ultrasound diagnosis apparatus according to the modification example is able to cause the waveform of the ultrasound wave output from the transducer element 30 to be substantially the same as the waveform indicated by the waveform signal.

Further, by allowing the current values of the constant current circuits 21a and 25a to be variable, it is possible to enhance the resolution and the precision level of the transmission waveform. For example, when a normal B-mode imaging method is used, the constant current circuits 21a and 25a are configured as constant current circuits of 10 mA, so that a current of 1000 mA at a maximum flows using the 100 constant current circuits. In contrast, when a contrast enhanced mode is used by which transmission is carried out with low power so as not to destruct microbubbles, the constant current circuits 21a and 25a are configured as constant current circuits of 1 mA, so as to be able to enhance the precision level of the waveform with the flow of a current of 100 mA at a maximum.

In yet another example, the switching element controlling circuit 18c may be configured to control the switching element 23 to be in the conductive state during the ultrasound wave transmission period (i.e., between the times t0 and t14). Further, the switching element controlling circuit 18c may be configured to control the switching element 23 to be in the non-conductive state in any time period other than the ultrasound wave transmission period. For example, the switching element controlling circuit 18c may be configured to keep applying negative voltage with respect to the source, to the gate of the switching element 23, in the duration from a time earlier than the time t0 by a short length of time Δt, to a time later than the time t14 by the short length of time Δt.

Similarly, the switching element controlling circuit 19c may be configured to control the switching element 27 to be in the conductive state during the ultrasound wave transmission period. Further, the switching element controlling circuit 19c may be configured to control the switching element 27 to be in the non-conductive state in any time period other than the ultrasound wave transmission period. For example, the switching element controlling circuit 19c may be configured to keep applying positive voltage with respect to the source, to the gate of the switching element 27, in the duration from the time earlier than the time t0 by the short length of time Δt to the time later than the time t14 by the short length of time Δt.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 150. Alternatively, instead of saving the programs in the memory 150, it is also acceptable to directly incorporate the programs into the circuits of the one or more processors. In that situation, the one or more processors realize the functions by reading and executing the programs incorporated in the circuits thereof. The processors according to the present embodiment do not each necessarily have to be structured as a single circuit. It is also acceptable to structure one processor by combining together a plurality of independent circuits, so as to realize the functions thereof. Further, two or more of the circuits (e.g., the signal processing circuit 130, the image generating circuit 140, and the controlling circuit 160) illustrated in FIG. 1 may be integrated in a single processor so as to realize the functions thereof. In other words, the signal processing circuit 130, the image generating circuit 140, and the controlling circuit 160 may be integrated into one processing circuit realized with the processor. Further, the controlling circuit 18 and the controlling circuit 19 may be realized by a single controlling circuit realized with a processor.

According to at least one aspect of the embodiments and the modification examples described above, it is possible to suppress the power consumption.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A transmission circuit comprising:
a plurality of constant current circuits connected in parallel to a power source line connected to a single power source and a transducer element;
a plurality of switching elements each of which is connected to a different one of the plurality of constant current circuits and to the transducer element; and
controlling circuitry configured to control the plurality of switching elements on a basis of a waveform signal indicating a waveform of an ultrasound wave output from the transducer element.

2. The transmission circuit according to claim 1, wherein each of the plurality of switching elements is configured to set an electrical connection state between a corresponding one of the plurality of constant current circuits and the transducer element to be in one selected from between a first state in which the corresponding one of the plurality of constant current circuits is electrically connected to the transducer element and a second state in which a connection between the corresponding one of the plurality of constant current circuits and the transducer element is electrically blocked, and
on the basis of the waveform signal, the controlling circuitry causes each of the plurality of switching elements to set the connection state between the corresponding one of the plurality of constant current circuits and the transducer element to be in the one of the first and the second states.

3. The transmission circuit according to claim 2, wherein the controlling circuitry causes the connection state to be set in the one of the first and the second states so that an ultrasound wave having the waveform indicated by the waveform signal is transmitted from the transducer element in a cycle of the waveform indicated by the waveform signal.

4. The transmission circuit according to claim 1, wherein at least one of a plurality of constant current values output from the plurality of constant current circuits is different from other values.

5. The transmission circuit according to claim 4, wherein a quantity of the plurality of constant current circuits is a smallest quantity among quantities of the constant current circuits capable of causing the waveform indicated by the waveform signal to be output from the transducer element.

6. An ultrasound diagnosis apparatus that includes a transmission circuit comprising:
a plurality of constant current circuits connected in parallel to a power source line connected to a single power source and a transducer element;
a plurality of switching elements each of which is connected to a different one of the plurality of constant current circuits and to the transducer element; and
controlling circuitry configured to control the plurality of switching elements on a basis of a waveform signal indicating a waveform of an ultrasound wave output from the transducer element.

* * * * *